(12) United States Patent
Jeong

(10) Patent No.: US 12,128,160 B2
(45) Date of Patent: Oct. 29, 2024

(54) AIR STERILIZATION DEVICE

(71) Applicant: ATIX CO., Ltd., Seongnam-si (KR)

(72) Inventor: Youn Mo Jeong, Gwangju-si (KR)

(73) Assignee: ATIX CO., LTD., Seongnam-si (KR)

( * ) Notice: Subject to any disclaimer, the term of this patent is extended or adjusted under 35 U.S.C. 154(b) by 371 days.

(21) Appl. No.: 17/544,009

(22) Filed: Dec. 7, 2021

(65) Prior Publication Data

US 2022/0211895 A1 Jul. 7, 2022

(30) Foreign Application Priority Data

Jan. 5, 2021 (KR) .................. 10-2021-0000941
Jun. 10, 2021 (KR) .................. 10-2021-0075606

(51) Int. Cl.
*A61L 9/20* (2006.01)
(52) U.S. Cl.
CPC ............ *A61L 9/20* (2013.01); *A61L 2209/111* (2013.01); *A61L 2209/20* (2013.01)
(58) Field of Classification Search
CPC .. A61L 9/20; A61L 2209/111; A61L 2209/20; F24F 8/22
See application file for complete search history.

(56) References Cited

U.S. PATENT DOCUMENTS

| | | | |
|---|---|---|---|
| 7,498,004 B2 | 3/2009 | Saccomanno | |
| 7,692,170 B2 | 4/2010 | Gaus et al. | |
| 9,023,274 B2 | 5/2015 | Garner et al. | |
| 9,555,144 B2 | 1/2017 | Garner et al. | |
| 9,821,259 B2 | 11/2017 | Bae et al. | |
| 9,950,088 B2 | 4/2018 | Garner et al. | |
| 10,406,254 B2 | 9/2019 | Garner et al. | |
| 10,406,470 B2 | 9/2019 | Bae et al. | |
| 10,413,857 B2 | 9/2019 | Bae et al. | |
| 11,090,598 B2 | 8/2021 | Bae et al. | |
| 11,219,700 B2 | 1/2022 | Garner et al. | |
| 11,666,846 B2 | 6/2023 | Bae et al. | |
| 2002/0098127 A1 | 7/2002 | Bollini | |
| 2003/0086848 A1 | 5/2003 | Saccomanno | |
| 2007/0214986 A1 | 9/2007 | Gaus et al. | |

(Continued)

FOREIGN PATENT DOCUMENTS

| | | |
|---|---|---|
| CN | 1610562 | 4/2005 |
| CN | 101027185 | 8/2007 |

(Continued)

*Primary Examiner* — David A Vanore
(74) *Attorney, Agent, or Firm* — LEX IP MEISTER, PLLC

(57) ABSTRACT

An air sterilization device includes a reflector, a first LED light source, and a second LED light source. The reflector may include a body part having a circular column shape having a vacant space therein and having openings formed in upper and lower surfaces thereof, a first rotary body connected to a lower surface of the body part and shaped to have a vacant space therein, and a second rotary body connected to an upper surface of the body part and shaped to have a vacant space; a first LED light source may emit UV-C rays in a direction from the first rotary body to the body part; and a second LED light source may emit UV-C rays in a direction from the second rotary body to the body part, and the reflector may reflect the light emitted from the first LED light source and the light emitted from the second LED light source.

17 Claims, 14 Drawing Sheets

(56) References Cited

U.S. PATENT DOCUMENTS

| | | |
|---|---|---|
| 2013/0243647 A1 | 9/2013 | Garner et al. |
| 2015/0217012 A1 | 8/2015 | Garner et al. |
| 2016/0214592 A1 | 7/2016 | Leroy et al. |
| 2017/0100500 A1 | 4/2017 | Garner et al. |
| 2017/0246580 A1 | 8/2017 | Bae et al. |
| 2017/0320002 A1 | 11/2017 | Bae et al. |
| 2017/0320003 A1 | 11/2017 | Bae et al. |
| 2019/0351084 A1 | 11/2019 | Garner et al. |
| 2019/0351357 A1 | 11/2019 | Bae et al. |
| 2020/0140291 A1 | 5/2020 | Babaie et al. |
| 2021/0338866 A1* | 11/2021 | Grenon ............... A61L 2/26 |
| 2021/0339181 A1 | 11/2021 | Bae et al. |
| 2021/0369906 A1* | 12/2021 | Ellis ............... A62B 18/08 |
| 2022/0111098 A1 | 4/2022 | Garner et al. |
| 2023/0086023 A1 | 3/2023 | Lai et al. |

FOREIGN PATENT DOCUMENTS

| | | |
|---|---|---|
| CN | 201439877 | 4/2010 |
| CN | 206398859 | 8/2017 |
| CN | 107865973 | 4/2018 |
| CN | 208747684 | 4/2019 |
| CN | 110944679 | 3/2020 |
| CN | 111623314 | 9/2020 |
| CN | 211875735 | 11/2020 |
| JP | H11-319817 | 11/1999 |
| KR | 10-0503258 | 7/2005 |
| KR | 10-2015-0014822 | 2/2015 |
| KR | 10-2020-0035618 | 4/2020 |
| KR | 10-2182402 | 11/2020 |
| KR | 10-2191549 | 12/2020 |
| KR | 10-2191577 | 12/2020 |

* cited by examiner

AIR STERILIZATION DEVICE

CROSS-REFERENCE TO RELATED APPLICATION

This application claims priority to and the benefit of Korean Patent Application No. 10-2021-0000941 filed in the Korean Intellectual Property Office on Jan. 5, 2021, and Korean Patent Application No. 10-2021-0075606 filed in the Korean Intellectual Property Office on Jun. 10, 2021, the entire contents of which are incorporated herein by reference.

BACKGROUND OF THE INVENTION

(a) Field of the Invention

The present disclosure relates to an air sterilization device.

(b) Description of the Related Art

Air cleaners in the related art are mostly mounted with H11 HEPA filters and purify air. The H11 HEPA filter has dust collecting efficiency of 95% based on a particle size of 0.3 um. However, because a size of a corona virus circulating worldwide in recent times is 0.08 to 0.1 um and smaller than a standard dust collecting size of the HEPA filter, the corona virus may pass through the HEPA filter. That is, the virus cannot be blocked only by the HEPA filter.

A sterilization method in the related art has been implemented by a catalyst reaction or an ozone reaction. However, because uniformity is hardly ensured in an effective sterilization region only by the catalyst reaction, there may be viruses that pass through the effective sterilization region without being sterilized. The ozone reaction is not appropriate to the daily life because of harmfulness of components thereof.

A UV lamp may more assuredly ensure a sterilization effect, but the technology related to the UV lamp is rejected because the UV lamp contains harmful substances such as mercury during a process of manufacturing the UV lamp. Some products perform the sterilization using UV LED light sources, but the UV LED light source is still insufficient to achieve the natural purpose of air sterilization.

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide an air sterilization device capable of providing sterilizing power sufficient to remove harmful microorganisms as well as corona viruses.

An exemplary embodiment of the present invention provides an air sterilization device including a reflector, a first LED light source, and a second LED light source. The reflector may include a body part having a circular column shape having a vacant space therein and having openings formed in upper and lower surfaces thereof, a first rotary body connected to a lower surface of the body part and shaped to have a vacant space therein, and a second rotary body connected to an upper surface of the body part and shaped to have a vacant space therein; the first LED light source may emit UV-C rays in a direction from the first rotary body to the body part; and a second LED light source may emit UV-C rays in a direction from the second rotary body to the body part, and the reflector may reflect the light emitted from the first LED light source and the light emitted from the second LED light source.

The first rotary body may have a first opening that faces an opening through which the first rotary body and the lower surface of the body part are connected, and the first LED light source may be positioned correspondingly to the first opening.

The second rotary body may have a second opening that faces an opening through which the second rotary body and the upper surface of the body part are connected, and the second LED light source may be positioned correspondingly to the second opening.

A length in an extension direction of the body part and a radius of the body part may be set so that a residence time, which is a time for which air resides in the air sterilization device, is equal to or longer than a predetermined sterilization time.

The length in the extension direction of the body part and the radius of the body part may be set so that minimum illuminance required to ensure predetermined sterilizing power may be provided to the air sterilization device. The predetermined sterilization time may be 0.07 seconds, the minimum illuminance may be 43 $mW/cm^2$, the length in the extension direction of the body part may be 80 mm to 120 mm, and the radius of the body part may be 25 mm to 35 mm.

A length of the first rotary body in a direction identical to an extension direction of the body part may be 5% to 15% of a length in an extension direction of the body part.

A length of the second rotary body in a direction identical to an extension direction of the body part may be 5% to 15% of a length in an extension direction of the body part.

An inclination angle of an inclined surface between a first opening of the first rotary body and an opening connected to the lower surface of the body part and facing the first opening may be 35 degrees to 55 degrees with respect to the lower surface of the body part.

An inclination angle of an inclined surface between a second opening of the second rotary body and an opening connected to the upper surface of the body part and facing the second opening may be 35 degrees to 55 degrees with respect to the upper surface of the body part.

The air sterilization device may further include a first heat sink coupled to the first LED light source; and a second heat sink coupled to the second LED light source.

The air sterilization device may further include a fan positioned on a lower portion of the first rotary body and configured to introduce air, in which the air introduced by the fan is introduced into the reflector through the first heat sink, passes through the body part, and is discharged to the outside of the reflector through the second heat sink.

Another exemplary embodiment of the present invention provides an air sterilization device including: a reflector implemented to have a shape made by coupling a body part and first and second rotary bodies coupled to two opposite surfaces of the body part, in which the body part has a vacant space therein, the first and second rotary bodies each have a vacant space therein, the first rotary body includes one surface connected to one of the two opposite surfaces of the body part, and the second rotary body includes one surface connected to the other of the two opposite surfaces of the body part. The air sterilization device may include a first LED light source positioned correspondingly to a first opening facing one surface of the first rotary body and configured to emit UV-C rays into the reflector; and a second LED light source positioned correspondingly to a second opening facing one surface of the second rotary body and configured to emit UV-C rays into the reflector.

A third opening facing the first opening may be formed in one surface of the first rotary body, and a fourth opening facing the second opening may be formed in one surface of the second rotary body.

The first LED light source may be positioned between the first opening and the third opening, and the second LED light source may be positioned between the second opening and the fourth opening.

The first and second LED light sources may be simultaneously turned on or only one of the first and second LED light sources may be turned on depending on a state of air.

The first and second LED light sources may be alternately turned off and on.

The present invention provides the air sterilization device capable of providing sterilizing power sufficient to remove harmful microorganisms as well as corona viruses.

DETAILED DESCRIPTION OF THE EMBODIMENTS

Figure 1:
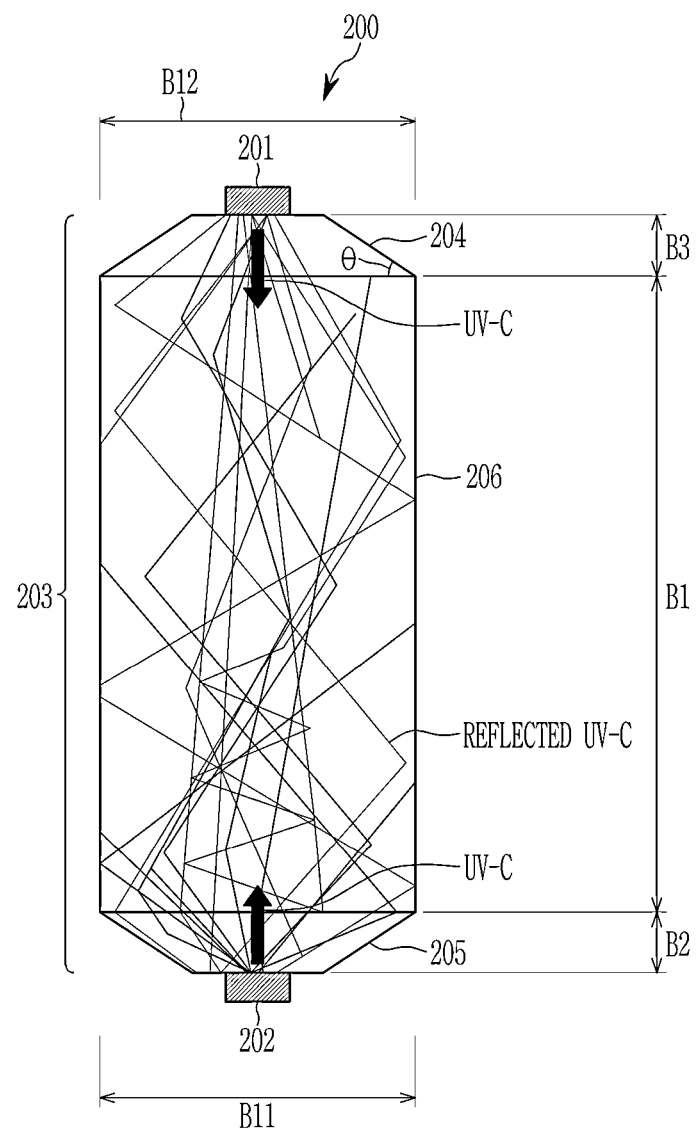
FIG. 1 is a view schematically illustrating an air sterilization device according to an embodiment.

The present invention relates to an air sterilization device using a UV LED light source and a reflector. Hereinafter, embodiments disclosed in the present specification will be described in detail with reference to the accompanying drawings. The same or similar constituent elements are assigned with the same or similar reference numerals, and the repetitive description thereof will be omitted. The suffixes 'module', 'unit', 'part', and/or 'portion' used to describe constituent elements in the following description are used together or interchangeably in order to facilitate the description, but the suffixes themselves do not have distinguishable meanings or functions. In addition, in the description of the exemplary embodiment disclosed in the present specification, the specific descriptions of publicly known related technologies will be omitted when it is determined that the specific descriptions may obscure the subject matter of the exemplary embodiment disclosed in the present specification. In addition, it should be interpreted that the accompanying drawings are provided only to allow those skilled in the art to easily understand the exemplary embodiments disclosed in the present specification, and the technical spirit disclosed in the present specification is not limited by the accompanying drawings, and includes all alterations, equivalents, and alternatives that are included in the spirit and the technical scope of the present invention.

The terms including ordinal numbers such as 'first', 'second', and the like may be used to describe various constituent elements, but the constituent elements are not limited by the terms. These terms are used only to distinguish one constituent element from another constituent element.

When one constituent element is described as being "coupled" or "connected" to another constituent element, it should be understood that one constituent element can be coupled or connected directly to another constituent element, and an intervening constituent element can also be present between the constituent elements. When one constituent element is described as being "coupled directly to" or "connected directly to" another constituent element, it should be understood that no intervening constituent element is present between the constituent elements.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

The embodiment of the present invention relates to an air sterilization device. For example, the air sterilization device includes an LED light source mounted in an air cleaner and configured to emit UV-C rays in a wavelength band of 100 to 280 nm instead of a catalyst or ozone reaction in the related art. The air passing through the interior of the air cleaner is irradiated directly with ultraviolet rays emitted from a UV-C LED light source, such that DNA or biological tissue of viruses, bacteria, and other harmful microorganisms contained in the air is destroyed and inactivated, thereby maintaining a user's health. The air sterilization device may be utilized by being mounted in the air cleaner or other small-sized portable products. For example, a small-sized air sterilization module may be manufactured and sized to be mounted in a small-sized or portable product, for example, an air cleaner, an AI speaker, a plant pot, a water tub, or the like and provide an air sterilization function.

FIG. 1 is a view schematically illustrating an air sterilization device according to an embodiment.

As illustrated in FIG. 1, an air sterilization device 200 includes two LED light sources 201 and 202 and a reflector 203. The reflector 203 illustrated in FIG. 1 includes a first rotary body 204, a second rotary body 205, and a body part 206 which is an effective sterilization region between the first rotary body 204 and the second rotary body 205. The reflector 203 defines an internal space of the air sterilization device 200. As illustrated in FIG. 1, UV-C rays are reflected in the internal space, thereby providing a sterilization action.

In FIG. 1, the two LED light sources 201 and 202 may each be implemented as a UV-C LED light source that makes an output of 10 mW or higher for the air sterilization. The two LED light sources 201 and 202 are disposed at two opposite ends of the reflector 203 so as to face each other. As described above, to achieve the air sterilization, the air sterilization device 200 according to the embodiment includes the reflector 203, and the two UV-C LED light sources 201 and 202 disposed in the reflector 203 so as to face each other.

The reflector 203 may be made of aluminum capable of effectively reflecting the ultraviolet rays. The reflector 203 may be made of a material such as stainless steel (stainless use steel (SUS), aluminum, Teflon, and the like) which is not a perfect absorber. Aluminum may be effective in consideration of costs and UV-C reflectance. The reflector changes the direction of the light so that the light exiting the LED light sources 201 and 202 enters the air sterilization device 200 again to apply the UV-C rays to the sterilization function, thereby contributing to the sterilizing power.

The UV-C LED light sources 201 and 202 make an output of at least 10 mW or higher in order to ensure the sufficient sterilization effect. Each of the UV-C LED light sources 201 and 202 is positioned at one of two opposite ends of the effective sterilization region in the reflector 203. The two UV-C LED light sources 201 and 202 are respectively positioned at positions corresponding to the two opposite ends of the effective sterilization region in the reflector 203 and disposed to face each other. A device for fixing the UV-C LED light sources 201 and 202 supports and fixes the UV-C LED light source. Electric wires and a temperature sensor for measuring a temperature may be provided on the device for fixing the UV-C LED light sources 201 and 202. For example, the temperature sensor positioned on the device measures a temperature of a surface of the reflector 203. It is possible to calculate and analogize temperatures of the UV-C LED light sources 201 and 202 by applying a regression equation to the measured temperature of the surface of the reflector.

Depending on a user's manipulation or distribution density of sterilization targets distributed in the air, the two LED light sources 201 and 202 may operate simultaneously or alternately or only the single LED light source may operate.

For example, in a case in which maximum sterilizing power needs to be ensured because a state of air measured by a dust sensor is very wrong, the two LED light sources 201 and 202 may be simultaneously turned on. When the state of air is good, one LED light source may be turned on, and the other LED light source may be turned off, thereby minimizing power consumption. Alternatively, from the state in which the first LED light source is turned on and the second LED light source is turned off, the first LED light source may be turned off and the second LED light source may be turned on, or the operation in the reverse order may be repeatedly performed, thereby minimizing a load applied to the LED light sources and minimizing the amount of heat generated from the LED light sources. The direct current (DC) voltage may be supplied to the LED light source to turn on the LED light source. Alternatively, the pulse voltage may be supplied to the LED light source, such that the LED light source may be repeatedly turned on and off.

The reflector 203 effectively disperses the ultraviolet rays generated therein, instead of light provided from the outside, without a missing part. The ultraviolet rays generated by the UV-C LED light source are reflected by the reflector 203, such that the interior of the reflector 203 is densely filled with the ultraviolet rays without a missing part. Therefore, intensity of a critical dose or more of ultraviolet rays required for sterilization may be ensured in the reflector 203. In addition, the two UV-C LED light sources, which are disposed to face each other, may ensure uniformity of intensity of the ultraviolet rays in the effective sterilization region in the reflector 203.

The reflector 203 may be implemented by coupling the body part 206 and the first and second rotary bodies 204 and 205. The body part 206 is provided in the form of a circular or polyhedral column having a vacant space therein, and the first and second rotary bodies 204 and 205 are disposed at two opposite ends of the body part 206 and each have a vacant space therein. An upper side of each of the first and second rotary bodies 204 and 205, which is positioned toward the outside of the air sterilization device, may be opened. The first and second rotary bodies 204 and 205 each have a shape truncated at a particular position thereof in a direction perpendicular to an axial direction of a cone. Alternatively, the first and second rotary bodies 204 and 205 may each have a shape made by rotating an equilateral trapezoid about a centerline that connects a center of an upper side and a center of lower side of the equilateral trapezoid. Therefore, a lateral surface (hereinafter, referred to as an 'inclined surface') of each of the first and second rotary bodies 204 and 205 is inclined at a particular angle with respect to a reference plane (e.g., an upper surface or a lower surface of the body part). Hereinafter, an angle at which the lateral surface of the first and second rotary bodies 204 and 205 is inclined is referred to as an 'inclination angle. Air is introduced into the reflector 203 through the opening of one of the first and second rotary bodies 204 and 205 and discharged to the outside through the opening of the other of the first and second rotary bodies 204 and 205. The interior of the reflector 203 may be made of a material capable of reflecting the ultraviolet rays, and a ratio between lengths B2 and B3 of the rotary bodies and a length B1 of the body part may be calculated depending on a field of view (FOV) of the LED light sources. The ultraviolet rays emitted from the LED light sources may be effectively dispersed depending on this ratio, thereby ensuring sterilizing power and uniformity for a target. The inclination angle is defined as an angle within a predetermined range based on the FOV of the LED light source, such that the components of the ultraviolet rays, which scatter backward, may be reflected and returned back to the effective sterilization region.

Figure 2:
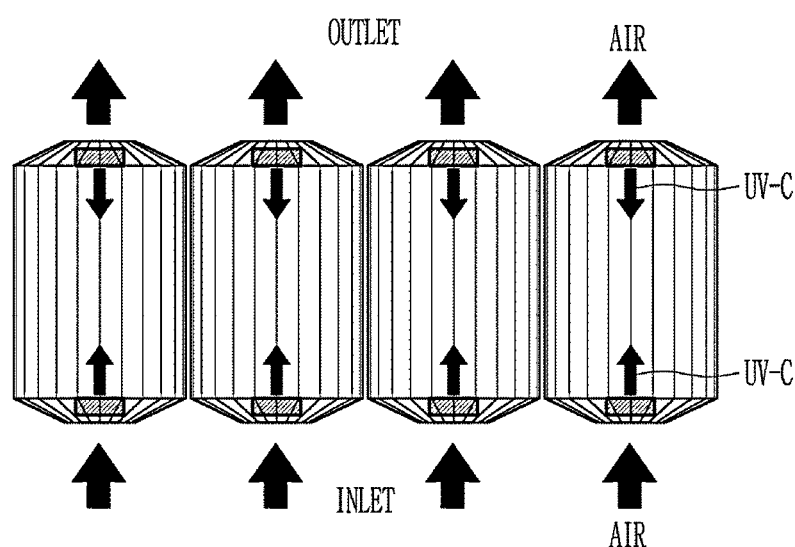
FIG. 2 is a view schematically illustrating an air cleaning system according to the embodiment.

FIG. 2 is a view schematically illustrating an air cleaning system according to the embodiment.

As illustrated in FIG. 2, a plurality of air sterilization devices is arranged to provide large-scale air sterilization.

Figure 3:
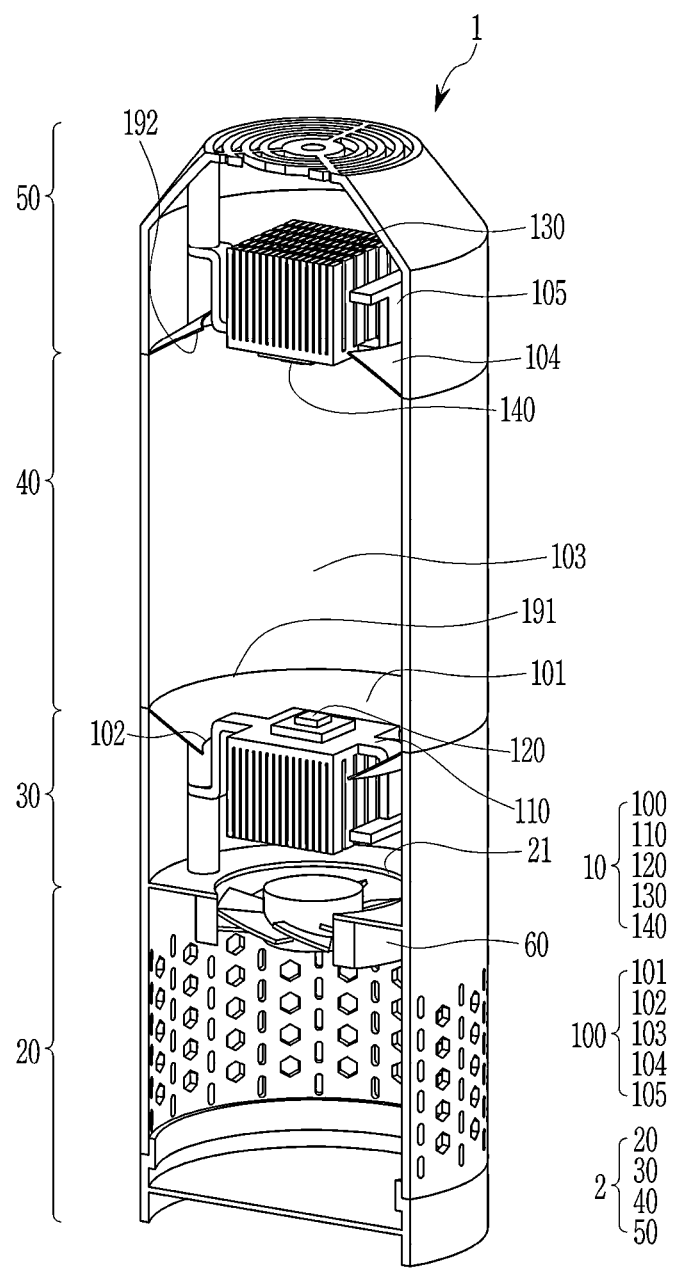
FIG. 3 is a view illustrating an air cleaner according to the embodiment.

FIG. 3 is a view illustrating an air cleaner according to the embodiment. FIG. 3 is a view illustrating an interior of an air cleaner 1 by cutting a predetermined part of the air cleaner 1 for clearly explaining a structure of an air sterilization device 10.

The air sterilization device 10 includes a reflector 100, heat sinks 110 and 130, and LED light sources 120 and 140. The reflector 100 includes a first rotary body 101, a first opening 102, a body part 103, a second rotary body 104, and a second opening 105. The first rotary body 101, the body part 103, and the second rotary body 104 may each be made of aluminum having a reflection function.

The body part 103 has a circular column shape having a vacant space therein and openings formed in upper and lower surfaces thereof.

Substantially, the upper and lower surfaces of the body part 103 may each include an opened region which is the entire region except for a rim region defined by a thickness of a lateral surface of the body part 103. The first rotary body 101 has a first opening 102, and the first rotary body 101 includes an upper surface that is connected to and in contact with a lower surface of the body part 103. The upper surface of the first rotary body 101 may have an opening 191 that is the entire region except for the rim region defined by a thickness of the inclined surface of the first rotary body 101. The second rotary body 104 has a second opening 105, and the second rotary body 104 includes a lower surface that is connected to and in contact with an upper surface of the body part 103. The lower surface of the second rotary body 104 may include an opening 192 which is the entire region except for the rim region defined by a thickness of the inclined surface of the second rotary body 104.

As illustrated in FIG. 3, the air cleaner 1 includes the air sterilization device 10, and a housing 2 that accommodates the air sterilization device 10. The housing 2 may include an air inflow part 20, a lower coupling part 30, a body cover part 40, and an upper coupling part 50. The lower coupling part 30 is coupled to the first rotary body 101 by means of a fastening means and fixes and supports the reflector 100. The upper coupling part 50 is coupled to the second rotary body 104 by means of a fastening means and fixes and supports the reflector 100. The body cover part 40 is disposed between the upper coupling part 50 and the lower coupling part 30 and surrounds the body part 103 of the reflector 100. The housing 2 has a circular column shape as a whole, but the present invention is not limited thereto. The air sterilization device has a shape including a circular column, and thus the housing 2 has a circular column shape as a whole. However, when the air sterilization device has a polyhedral column shape, the body cover part 40 of the housing 2 may at least have a polyhedral column shape. A lower structure 20 may have a circular column shape having a plurality of holes through which the outside air is introduced. An upper surface of the lower structure 20 has a circular opening 21 in which a fan 60 is positioned, and the fan 60 is coupled to a lower end of the circular opening 21. The outside air is introduced by the fan 60 and flows upward.

The LED light source 120 coupled to the heat sink 110 is positioned in the first opening 102 formed in the lower surface of the first rotary body 101 positioned at one end of the reflector 100. The LED light source 140 coupled to the heat sink 130 is positioned in the second opening 105 formed in the upper surface of the second rotary body 104 positioned at the other end of the reflector 100. A side of the LED light source 120, from which the light is radiated, may be positioned in a region defined by the length B2 of the first rotary body 101, and a side of the LED light source 140, from which the light is radiated, may be positioned in a region defined by the length B3 of the second rotary body 104.

The air introduced by the fan 60 is introduced into the reflector 100 through the heat sink 110, passes through the body part 103, and is discharged to the outside of the reflector 100 through the heat sink 130. A plurality of discharge ports is formed in an upper surface of the upper coupling part 50 positioned at the upper side of the reflector 100 so that the air may be discharged through the plurality of discharge ports. The discharge ports illustrated in FIG. 3 are each provided in the form of a circular band, but the present invention is not limited to this example.

Figure 4:
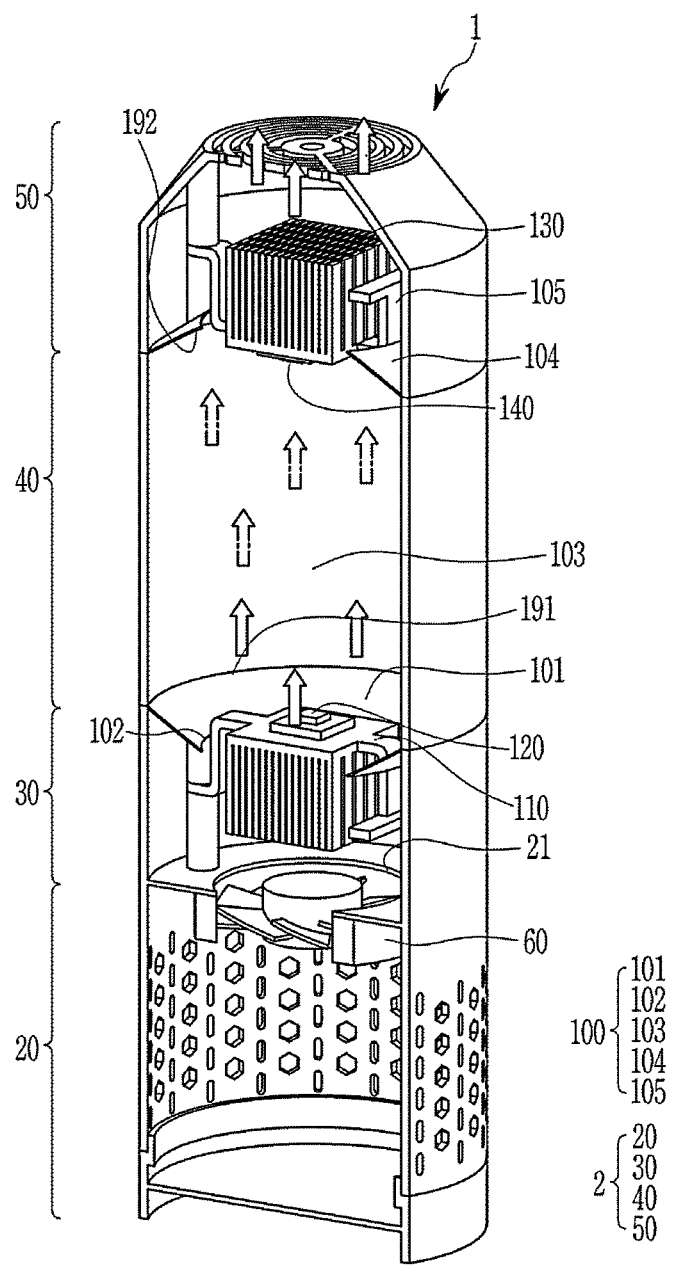
FIG. 4 is a view illustrating a flow of air introduced and discharged by the air cleaner.

FIG. 4 is a view illustrating a flow of air introduced and discharged by the air cleaner.

Figure 5:
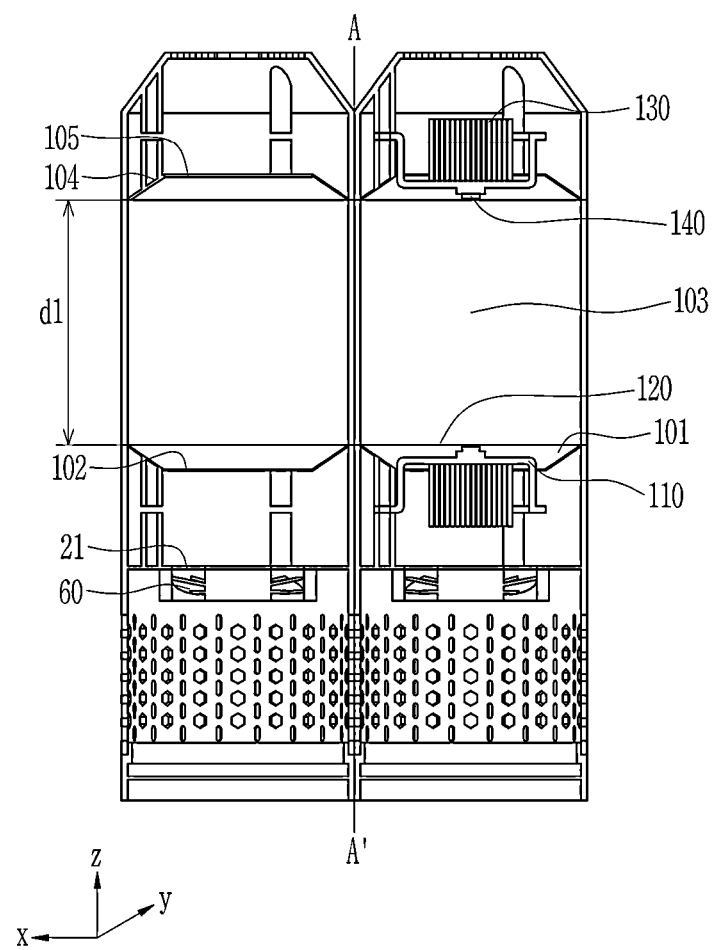
FIG. 5 is a view illustrating the air cleaner cut in half and opened with respect to A-A' axis.

FIG. 5 is a view illustrating the air cleaner cut in half and opened with respect to A-A' axis.

Figure 6:
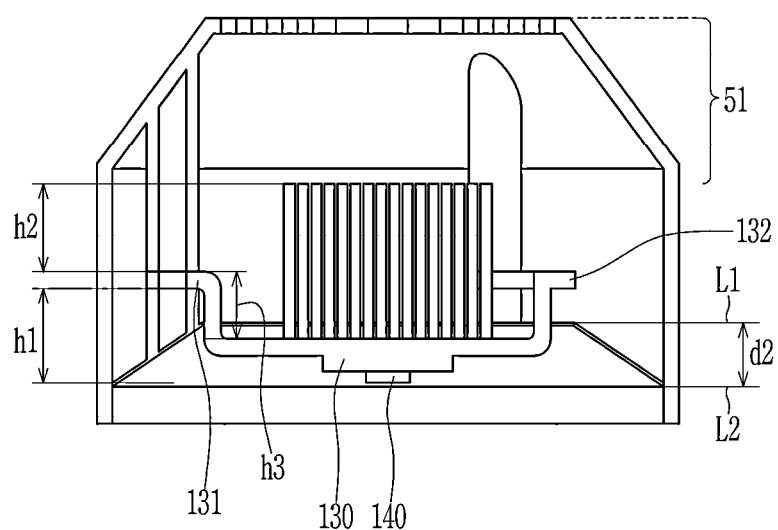
FIGS. 6 and 7 are views illustrating an upper coupling part in a right cross-section in FIG. 5.
Figure 7:
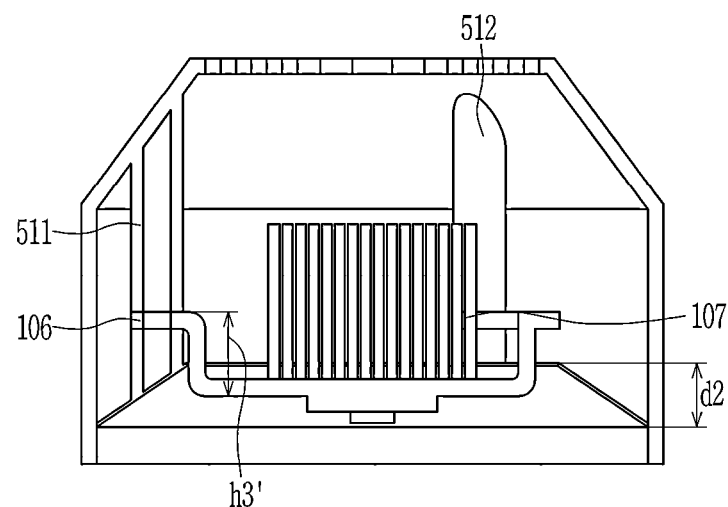

FIGS. 6 and 7 are views illustrating the upper coupling part in the right cross-section in FIG. 5.

Figure 8:
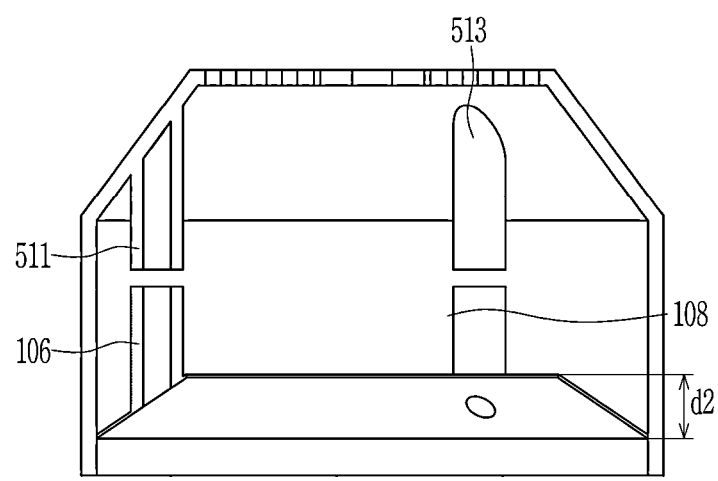
FIG. 8 is a view illustrating the upper coupling part in a left cross-section in FIG. 5.

FIG. 8 is a view illustrating the upper coupling part in the left cross-section in FIG. 5.

As illustrated in FIGS. 6 and 7, a cap 51 is a part of an upper coupled part 50 which is inclined at an angle corresponding to the second rotary body 104. h1 represents a length of a connection part 106 of the second rotary body 104 connected to a connection part 511 of the cap 51 by means of a fastening means and may be set to a length in a z-axis direction of the second rotary body 104. h2 represents a length of the connection part 511 extending downward in the z-axis direction from a lower surface of the cap 51 and may be set to a length in the z-axis direction of the cap 51.

h1 and h2 are fixed. Lengths in the z-axis direction of bridges 131 and 132 of the heat sink 130 are determined depending on a position of a light-emitting surface of the LED light source 140. For example, a light-emitting part of the LED light source 140 may be positioned in a range of distance d2 from a line L1 to a line L2. Then, a difference between a minimum value and a maximum value of a length h3 in the z-axis direction of the bridge 131 may be d2. In FIG. 6, a position of the light-emitting part of the LED light source 140 is adjacent to the line L1. In FIG. 7, a position of the light-emitting part of the LED light source 140 is adjacent to line L2. A difference between the length h3 in the z-axis direction of the bridge 131 illustrated in FIG. 6 and a length h3' in the z-axis direction of the bridge 131 illustrated in FIG. 7 may be a difference between the position of the light-emitting part of the LED light source 140 illustrated in FIG. 6 and the position of the light-emitting part of the LED light source 140 illustrated in FIG. 7.

Further, in the air sterilization device 10, the positions of the two heat sinks 110 and 130, the positions of the two LED light sources 120 and 140, and the positions of the first and second rotary bodies 101 and 104 may be symmetric with respect to the center of the air sterilization device 10.

In addition, in FIGS. 5, 6, and 7, a ratio between a length d1 in the z-axis direction of the body part 103 and a length d2 in the z-axis direction of the second rotary body 104 may be set to approximately 10:1.

Figure 9:
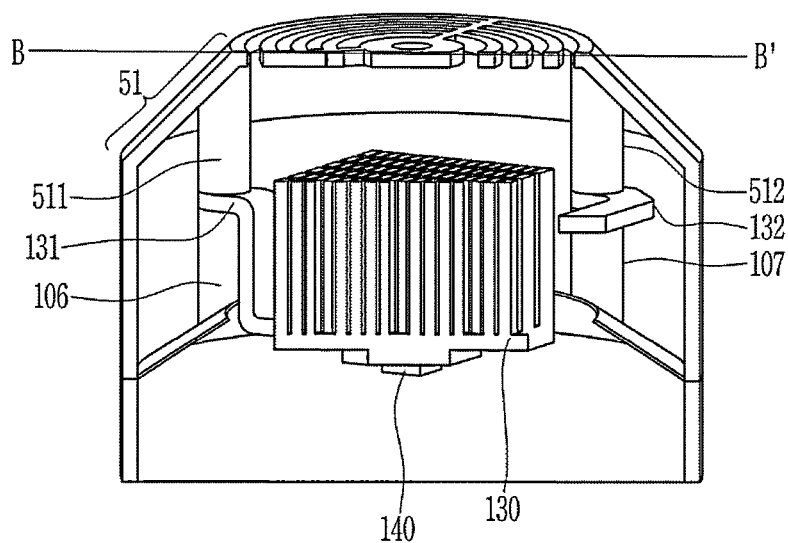
FIG. 9 is a cross-sectional view taken along line B-B' and illustrating an upper structure of the air cleaner.

FIG. 9 is a cross-sectional view taken along line B-B' and illustrating the upper structure of the air cleaner.

Figure 10:
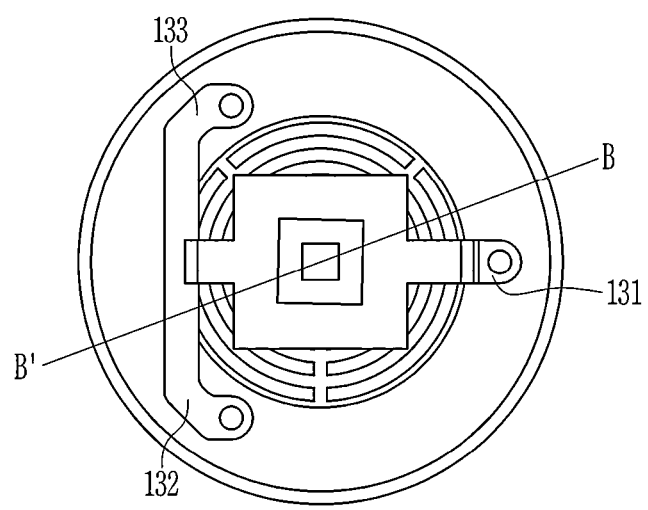
FIG. 10 is a view illustrating a heat sink coupled to the upper coupling part of the air cleaner when viewed from below to above in a z-axis direction.

FIG. 10 is a view illustrating the heat sink coupled to the upper coupling part of the air cleaner when viewed from below to above in the z-axis direction.

As illustrated in FIG. 10, the three bridges 131, 132, and 133 extending from the main body of the heat sink 130 are partially positioned between the three connection parts 511 and 512 in FIGS. 7 and 513 in FIG. 8 extending downward in the z-axis direction from the lower surface of the cap 51 and the three connection parts 106, 107, and 108 extending upward in the z-axis direction from the upper surface of the second rotary body 104. The connection part of the cap 51, the bridge, and the connection part of the second rotary body 104 are coupled and fixed by fastening means (e.g., screws).

A coupling structure between the lower coupling part 30 and the first rotary body 101 is similar to the above-mentioned coupling structure between the upper coupling part 50 and the second rotary body 104.

Figure 11:
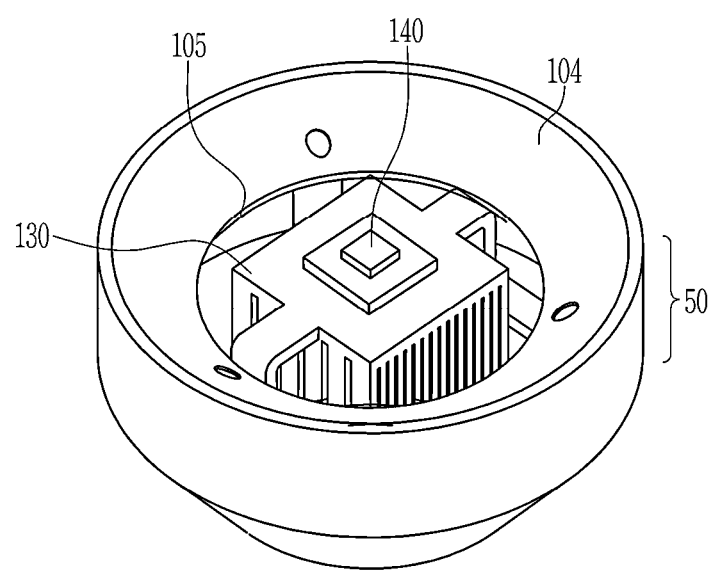
FIG. 11 is a perspective view illustrating a state in which the upper coupling part, the heat sink, and an LED light source of the air cleaner are coupled when viewed from below.

FIG. 11 is a perspective view illustrating a state in which the upper coupling part, the heat sink, and the LED light source of the air cleaner are coupled when viewed from below.

Figure 12:
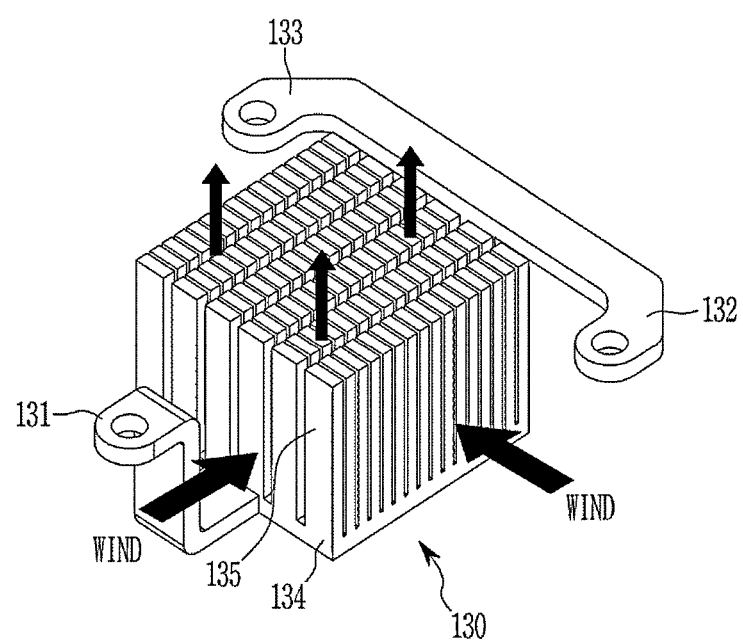
FIG. 12 is a view illustrating a flow of air in the heat sink.

FIG. 12 is a view illustrating a flow of air in the heat sink.

As illustrated in FIG. 12, the heat sink 130 has a plurality of fins (e.g., 135) extending in the z-axis direction from a lower structure 134. Then, wind passes through the heat sink 130 in all directions, thereby facilitating cooling. Further, the bridges 131, 132, and 133 extend from the lower structure 134.

Figure 13:
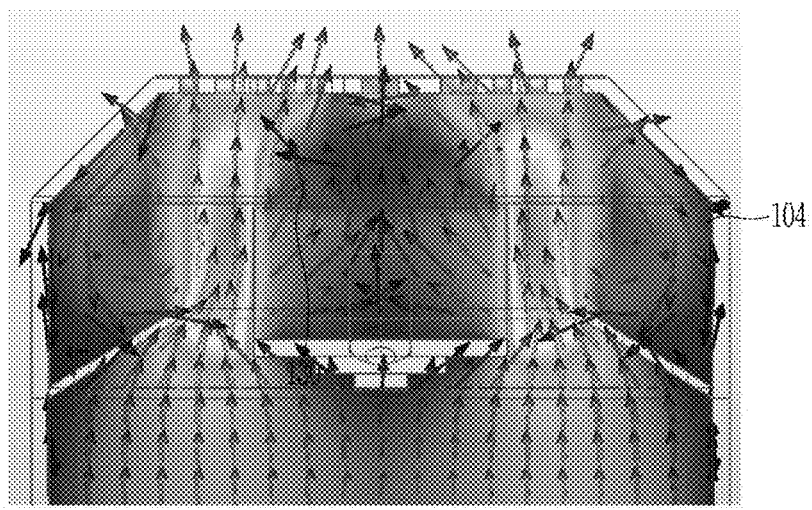
FIG. 13 is a view illustrating a flow of air in the upper coupling part.

FIG. 13 is a view illustrating a flow of air in the upper coupling part. As illustrated in FIG. 13, it can be seen that the air, which is discharged to a portion between the second rotary body 104 and the heat sink 130 is cooled by flowing into the heat sink 130.

The use of the present invention may establish the sterilization system capable of directly sterilizing the air and substantially removing corona viruses and other harmful microorganisms. The air sterilization device may be mounted in an air cleaner in the related art to develop the product capable of simultaneously removing fine dust and viruses. Alternatively, the air sterilization device may be mounted in the air cleaner using the advantage of the small-sized air sterilization device according to the present invention even though the product is not used for the purpose of sterilization. For example, the present module may be mounted in a predetermined space inside or outside a plant pot disposed for the purpose of indoor interior design, thereby obtaining the air sterilization effect.

The viruses such as COVID-19 may be sterilized by a smaller dose than colon bacilli. 1.89 dose is required for 99.99% sterilization of general colon bacilli. However, in the case of COVID-19, 99.9% sterilization is enabled at a level of 50% of colon bacillus sterilizing power. The sterilizing power of 3 doses or more needs to be ensured to prevent virus infection through the air that may occur in the future in addition to COVID-19.

The present embodiment may provide the compact air sterilization device that instantaneously provides the sterilizing power of 3 doses. To this end, optimized design is required for the LED light source and reflector structure of the air sterilization device. The following examples are provided to explain the present invention and does not limit the protection scope of the present invention.

When the length B1 of the body part, which corresponds to the length of the air sterilization device, decreases to miniaturize the air sterilization device, the miniaturization may be implemented, but the distance between the LED light sources decreases. In this case, heat generated from one LED light source affects the other LED light source, which affects the durability and reliability of the LED light source. In this case, the output of the LED light source decreases, which may cause a reduction in sterilizing power and a deterioration in performance of the air sterilization device.

In addition, the air sterilization device may be miniaturized by decreasing a diameter (B11 or B12 in FIG. 1) of the air sterilization device to miniaturize the air sterilization device. However, the time for which the air resides in the air sterilization device becomes shorter than the sterilization time required to ensure 99.9% sterilizing power. To ensure the sterilizing power while reducing the size of the air sterilization device, the time for which the air resides in the air sterilization device needs to be equal to or longer than a predetermined sterilization time (e.g., the sterilization time required to ensure 99.9% sterilizing power. In addition, minimum illuminance required to ensure 99.9% sterilizing power needs to be provided to the air sterilization device.

In the following description, various examples of the air sterilization device, which may minimize the size of the air sterilization device while satisfying the sterilizing power of 99.9% will be described. For example, to provide a function of performing 99.9% sterilization when the air passes through the air sterilization device 200 once, the air sterilization device 200 may be designed to satisfy a condition in which the minimum residence time of the air is 0.07 seconds and the minimum illuminance in the air sterilization device 200 is 43 mW/cm$^2$. The residence time refers to the time for which the air is introduced into one side of the air sterilization device 200 and discharged from the other side of the air sterilization device 200 in an ideal equilibrium state. That is, the residence time refers to the time for which the air passes through the interior of the air sterilization device 200. The minimum residence time may be set to 0.07 seconds. The minimum illuminance means the lowest illuminance in respect to intensity of the light emitted for each unit area in the air sterilization device 200. A critical value of the minimum illuminance may be 43 mW/cm$^2$. The minimum dose may be set to 3 mJ, i.e., a value made by multiplying the minimum residence time by the critical value of the minimum illuminance (0.07 seconds*43 mW/cm$^2$). When the minimum residence time increases or the minimum illuminance increases, the sterilizing power may increase as the minimum illuminance increases.

The residence time and the minimum illuminance value may be derived by flow analyses and optical simulations.

Table 1 shows the length B1 and ½ of B11 and B12 that satisfy the minimum residence time of 0.07 seconds.

TABLE 1

| Residence time for each condition (sec.) | | Radius of body part (½ of B11 and B12) [mm] | | | | |
| --- | --- | --- | --- | --- | --- | --- |
| | | 15 | 20 | 25 | 30 | 35 |
| Length of body part (B1) [mm] | 50 | 0.02 | 0.03 | 0.04 | 0.06 | 0.08 |
| | 60 | 0.02 | 0.03 | 0.05 | 0.07 | 0.10 |
| | 70 | 0.02 | 0.04 | 0.06 | 0.09 | 0.12 |
| | 80 | 0.02 | 0.04 | 0.07 | 0.10 | 0.13 |
| | 90 | 0.03 | 0.05 | 0.08 | 0.11 | 0.15 |
| | 100 | 0.03 | 0.05 | 0.09 | 0.12 | 0.17 |
| | 110 | 0.03 | 0.06 | 0.09 | 0.14 | 0.18 |
| | 120 | 0.04 | 0.066 | 0.10 | 0.15 | 0.20 |

However, in Table 1, when the length B1 of the body part is short (e.g., shorter than 80 mm), the distance between the two LED light sources 201 and 202, which is the light sources, is too short. Therefore, the two LED light sources 201 and 202 affect each other in terms of reliability and durability of the light sources. This may cause a deterioration in sterilizing power. In addition, to miniaturize the air sterilization device 200, the length B1 of the body part is set to 120 mm or less, and the radius (½ of B11 and B12) of the body part is set to 35 mm or less. Therefore, referring to Table 1, to satisfy the miniaturization and the minimum residence time, the length B1 of the body part may be designed in a range of 80 mm to 120 mm, and the radius (½ of B11 and B12) may be designed in a range of 25 mm to 35 mm.

Table 2 shows minimum illuminance and doses in the air sterilization device 200 under the structural conditions of the air sterilization device shown in Table 1.

TABLE 2

| Reference residence time | 0.07 | Radius of body part (½ of B11 and B12) [mm] | | | | | | | | |
|---|---|---|---|---|---|---|---|---|---|---|
| Minimum target illuminance | 43 | 15 | | | 20 | | | 25 | | |
| Minimum target dose | 3.01 | Residence time | Minimum illuminance | Dose | Residence time | Minimum illuminance | Dose | Residence time | Minimum illuminance | Dose |
| Length of body part (B1) [mm] | 50 | 0.02 | 90.09 | 1.38 | 0.03 | 74.08456 | 2.02 | 0.04 | 46.33923 | 1.98 |
| | 60 | 0.02 | 87.73 | 1.62 | 0.03 | 69.91362 | 2.29 | 0.05 | 45.52792 | 2.33 |
| | 70 | 0.02 | 87.89 | 1.89 | 0.04 | 70.59217 | 2.70 | 0.06 | 46.11983 | 2.75 |
| | 80 | 0.02 | 90.50 | 2.22 | 0.04 | 70.16261 | 3.07 | 0.07 | 46.74986 | 3.19 |
| | 90 | 0.03 | 86.43 | 2.39 | 0.05 | 67.89755 | 3.34 | 0.08 | 45.90056 | 3.52 |
| | 100 | 0.03 | 85.7887 | 2.64 | 0.05 | 65.96786 | 3.60 | 0.09 | 44.57061 | 3.80 |
| | 110 | 0.03 | 83.25767 | 2.81 | 0.06 | 62.5933 | 3.76 | 0.09 | 42.74401 | 4.01 |
| | 120 | 0.04 | 79.949 | 2.95 | 0.07 | 59.5764 | 3.90 | 0.10 | 40.87657 | 4.19 |

| Reference residence time | Radius of body part (½ of B11 and B12) [mm] | | | | | |
|---|---|---|---|---|---|---|
| Minimum target illuminance | 30 | | | 35 | | |
| Minimum target dose | Residence time | Minimum illuminance | Dose | Residence time | Minimum illuminance | Dose |
| Length of body part (B1) [mm] | 0.06 | 40.21906 | 2.47 | 0.06 | 31.83908 | 2.66 |
| | 0.07 | 38.24287 | 2.82 | 0.10 | 30.74466 | 3.09 |
| | 0.09 | 36.47883 | 3.14 | 0.12 | 31.55007 | 3.69 |
| | 0.10 | 38.23582 | 3.76 | 0.13 | 32.18431 | 4.31 |
| | 0.11 | 36.84734 | 4.07 | 0.15 | 31.45101 | 4.73 |
| | 0.12 | 35.56351 | 4.37 | 0.17 | 30.00329 | 5.02 |
| | 0.14 | 33.55328 | 4.53 | 0.18 | 27.38982 | 5.04 |
| | 0.15 | 32.35319 | 4.77 | 0.20 | 25.96985 | 5.21 |

As can be seen in Table 2, when the length B1 of the body part is 60 mm and the radius (½ of B11 and B12) of the air sterilization device is 35 mm, the reference minimum dose is satisfied. When the length B1 of the body part is 70 mm and the radius (½ of B11 and B12) of the air sterilization device is in a range of 30 mm to 35 mm, the reference minimum dose is satisfied. When the length B1 of the body part is 80 to 120 mm and the radius (½ of B11 and B12) of the air sterilization device is in a range of 20 mm to 35 mm, the reference minimum dose is satisfied.

Therefore, it can be seen that the design conditions of the minimum illuminance and the minimum residence condition described with reference to Table 1 are also satisfied.

The rotary bodies 204 and 205 serve to reflect the light emitted from the LED light sources 201 and 202 and transmit the light into the reflector 100. The light reflected by the rotary bodies 204 and 205 may contribute to the sterilization.

The shape of each of the rotary bodies 204 and 205 is related to the residence time for which the air resides in the internal space of the reflector 100. For example, the lengths B3 and B2 and the inclination angle of the rotary bodies 204 and 205 need to be designed so as not to reduce the residence time. For example, each of the lengths B3 and B2 of the rotary bodies 204 and 205 may be appropriately designed to have a length that is 10% of the length B1 of the body part. To cope with an assembly error and a change in residence time due to the assembly error, each of the lengths B3 and B2 of the rotary bodies 204 and 205 may be designed within a range of 5% to 15% of the length B1 of the body part.

Further, an inclination angle $\theta$ needs to be designed to have a value larger than 0 degree. The inclination angle $\theta$ may be designed to ensure the minimum residence time in consideration of the change in residence time in accordance with the inclination angle $\theta$ of each of the rotary bodies 204 and 205. The inclination angle $\theta$ may be designed to be 45 degrees in consideration of the probability of the light contributing to the sterilization in the reflector 100. The light emitted from the LED light sources 201 and 202 is reflected by the inclined surfaces of the rotary bodies 204 and 205, such that a direction vector of the light may be changed to a direction vector of the light perpendicular to the optical axis. The optical axis is the direction indicated by the arrows in FIG. 1. Therefore, the number of light beams, which are reflected by the inclined surfaces of the rotary bodies 204 and 205 and introduced into the reflector 100 among the light beams emitted from the LED light sources 201 and 202, is increased. The light beams entering the reflector 100 may contribute to the sterilization. The inclination angle $\theta$ may be designed with a margin of +/−10 degrees with respect to an angle of 45 degrees to correct the assembly tolerance and the system.

In the embodiment, the inclination angle has been described as 45 degrees, but the present invention is not limited thereto. The inclination angle may vary depending on the structure of the reflector 100, the lengths B2 and B3 of the rotary body, the length B1 of the body part, and the like. The light emitted from the LED light source may contribute directly to the sterilization in the reflector 100, and the light radiated from the LED light source may be reflected by the rotary body, thereby contributing to the sterilization. The inclination angle of the rotary body may be set such that a degree of the contribution to the sterilization by the reflection of the light emitted from the LED light source is maximized.

Figure 14:
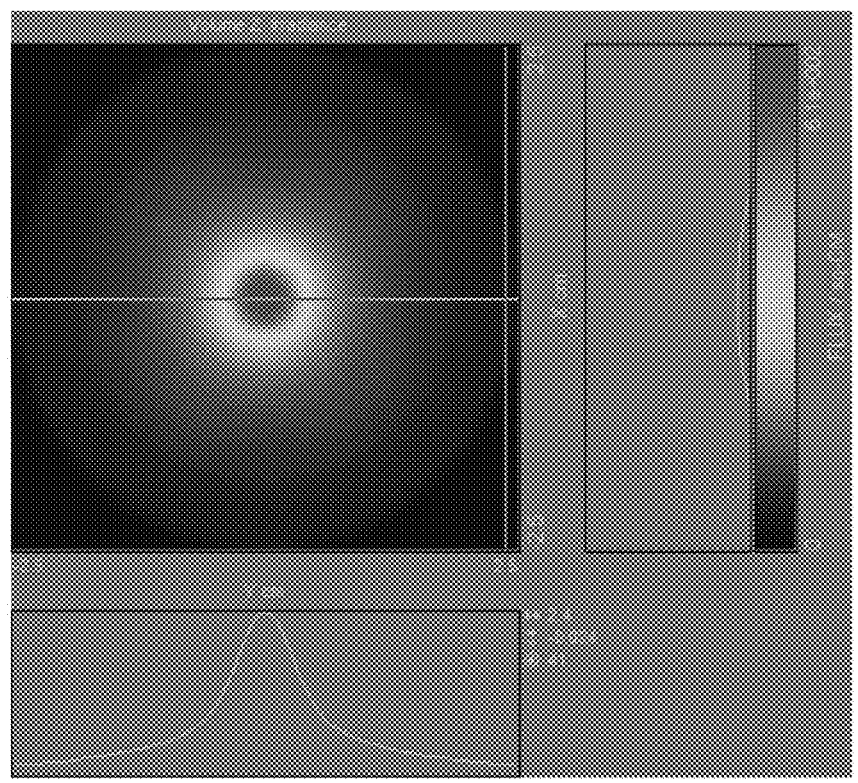
FIG. 14 is a view schematically illustrating illuminance values in a cross-section perpendicular to a longitudinal direction of a reflector according to the embodiment.

FIG. 14 is a view schematically illustrating illuminance values in a cross-section perpendicular to a longitudinal direction of the reflector according to the embodiment.

When the illuminance value illustrated in FIG. 14 is multiplied by the residence time in the reflector 100, the illuminance at the outermost periphery (the outermost periphery of the circular region illustrated in FIG. 14) of the reflector 100 is 40 mW/cm². The residence time in the reflector 100 according to the embodiment, which is calculated depending on the flow analysis, is approximately 0.1208 seconds. Therefore, an approximate dose at the outermost periphery in the reflector 100 is 4.9529 [dose]. FIG. 14 schematically illustrates that the illuminance value is an illuminance value in the reflector 100 when the inclination angle of the rotary body is 45 degrees, the length of the body part is 120 mm, and the length of the rotary body is 12 mm. The length of the rotary body corresponds to 10% of the length of the body part.

While the embodiments of the present invention have been described in detail above, the protection scope of the present invention is not limited thereto, various alterations and modifications may be made by those skilled in the art, and these alterations and modifications belong to the protection scope of the present invention.

DESCRIPTION OF SYMBOLS

1: Air cleaner
10, 200: Air sterilization device

What is claimed is:

1. An air sterilization device comprising:
a reflector comprising a body part having a circular column shape having a vacant space therein and having openings formed in upper and lower surfaces thereof, a first rotary body connected to a lower surface of the body part and shaped to have a vacant space therein, and a second rotary body connected to an upper surface of the body part and shaped to have a vacant space therein;
a first LED light source configured to emit UV-C rays in a direction from the first rotary body to the body part; and
a second LED light source configured to emit UV-C rays in a direction from the second rotary body to the body part,
wherein the reflector reflects the light emitted from the first LED light source and the light emitted from the second LED light source, and
wherein each of the first and second rotary bodies has a shape truncated at a particular position thereof in a direction perpendicular to an axial direction of a cone and a lateral surface of each of the first and second rotary bodies is inclined at a particular angle with respect to an upper surface and a lower surface of the body part, respectively.

2. The air sterilization device of claim 1, wherein:
the first rotary body has a first opening that faces an opening through which the first rotary body and the lower surface of the body part are connected, and
the first LED light source is positioned correspondingly to the first opening.

3. The air sterilization device of claim 1, wherein:
the second rotary body has a second opening that faces an opening through which the second rotary body and the upper surface of the body part are connected, and
the second LED light source is positioned correspondingly to the second opening.

4. The air sterilization device of claim 1, wherein:
a length in an extension direction of the body part and a radius of the body part are set so that a residence time, which is a time for which air resides in the air sterilization device, is equal to or longer than a predetermined sterilization time.

5. The air sterilization device of claim 4, wherein:
the length in the extension direction of the body part and the radius of the body part are set so that minimum illuminance required to ensure predetermined sterilizing power is provided to the air sterilization device.

6. The air sterilization device of claim 5, wherein:
the predetermined sterilization time is 0.07 seconds, the minimum illuminance is 43 mW/cm²,
the length in the extension direction of the body part is 80 mm to 120 mm, and
the radius of the body part is 25 mm to 35 mm.

7. The air sterilization device of claim 1, wherein:
a length of the first rotary body in a direction identical to an extension direction of the body part is 5% to 15% of a length in an extension direction of the body part.

8. The air sterilization device of claim 1, wherein:
a length of the second rotary body in a direction identical to an extension direction of the body part is 5% to 15% of a length in an extension direction of the body part.

9. The air sterilization device of claim 1, wherein:
an inclination angle of an inclined surface between a first opening of the first rotary body and an opening connected to the lower surface of the body part and facing the first opening is 35 degrees to 55 degrees with respect to the lower surface of the body part.

10. The air sterilization device of claim 1, wherein:
an inclination angle of an inclined surface between a second opening of the second rotary body and an opening connected to the upper surface of the body part and facing the second opening is 35 degrees to 55 degrees with respect to the lower surface of the body part.

11. The air sterilization device of claim 1, further comprising:
a first heat sink coupled to the first LED light source; and
a second heat sink coupled to the second LED light source.

12. The air sterilization device of claim 11, further comprising:
a fan positioned on a lower portion of the first rotary body and configured to introduce air,
wherein the air introduced by the fan is introduced into the reflector through the first heat sink, passes through the body part, and is discharged to the outside of the reflector through the second heat sink.

13. An air sterilization device comprising:
a reflector implemented to have a shape made by coupling a body part and first and second rotary bodies coupled to two opposite surfaces of the body part, wherein the body part has a vacant space therein, the first and second rotary bodies each have a vacant space therein, the first rotary body comprises one surface connected to one of the two opposite surfaces of the body part, and the second rotary body comprises one surface connected to the other of the two opposite surfaces of the body part;
a first LED light source positioned correspondingly to a first opening facing one surface of the first rotary body and configured to emit UV-C rays into the reflector; and a second LED light source positioned correspondingly to a second opening facing one surface of the second rotary body and configured to emit UV-C rays into the reflector, wherein each of the first and second rotary bodies has a shape truncated at a particular position thereof in a direction perpendicular to an axial direction of a cone and a lateral surface of each of the first and second rotary bodies is inclined at a particular angle with respect to an upper surface and a lower surface of the body part, respectively.

14. The air sterilization device of claim 13, wherein:

a third opening facing the first opening is formed in one surface of the first rotary body, and a fourth opening facing the second opening is formed in one surface of the second rotary body.

15. The air sterilization device of claim 14, wherein:

the first LED light source is positioned between the first opening and the third opening, and the second LED light source is positioned between the second opening and the fourth opening.

16. The air sterilization device of claim 13, wherein:

the first and second LED light sources are simultaneously turned on or only one of the first and second LED light sources is turned on depending on a state of air.

17. The air sterilization device of claim 13, wherein:

the first and second LED light sources are alternately turned off and on.

* * * * *